United States Patent [19]
Wood et al.

[11] Patent Number: 5,266,305
[45] Date of Patent: Nov. 30, 1993

[54] COPOLYMERS OF POLYAMINO ACIDS AS TARTAR BARRIER AGENTS

[75] Inventors: Louis L. Wood, Rockville; Gary J. Calton, Elkridge, both of Md.

[73] Assignee: SRCHEM Incorporated, Elkridge, Md.

[21] Appl. No.: 968,506

[22] Filed: Oct. 29, 1992

[51] Int. Cl.$^5$ .................. A61K 7/16; A61K 7/22
[52] U.S. Cl. ........................................ 424/54; 424/49
[58] Field of Search ............................. 424/49-58

[56] References Cited

U.S. PATENT DOCUMENTS

| | | | |
|---|---|---|---|
| 3,846,380 | 11/1974 | Fujimoto et al. | 260/78 A |
| 4,339,431 | 7/1982 | Gaffar | 424/54 |
| 4,362,713 | 12/1982 | Buck | 424/54 |
| 4,866,161 | 9/1989 | Sikes et al. | 530/324 |
| 4,868,287 | 9/1989 | Sikes et al. | 424/54 |
| 5,051,401 | 9/1991 | Sikes | 424/54 |
| 5,152,902 | 10/1992 | Koskan et al. | 210/698 |

OTHER PUBLICATIONS

Dunachy et al. C.A. 118:102483g (1993) of WO/PCT9217184 Oct. 15, 1992.

*Primary Examiner*—Shep K. Rose
*Attorney, Agent, or Firm*—William S. Ramsey

[57] ABSTRACT

Copolymers of polyamino acids formed by reaction of polysuccinimide with alkyl, alkenyl, aromatic amines or alkyl and alkenyl polyamines are useful as inhibitors of tartar deposition. Such compounds may be used in conventional dentifrice compositions to prevent tartar deposition on natural or false teeth.

8 Claims, 1 Drawing Sheet

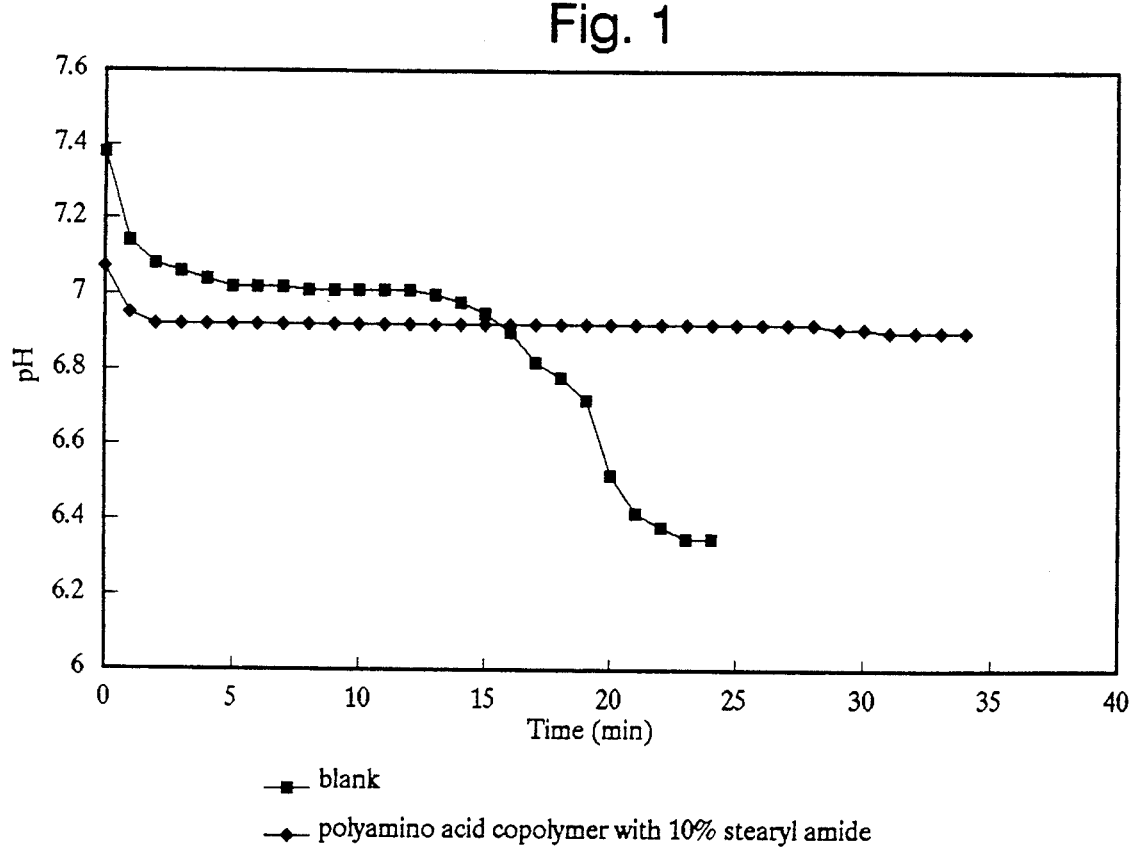

COPOLYMERS OF POLYAMINO ACIDS AS TARTAR BARRIER AGENTS

FIELD OF THE INVENTION

This invention relates to the use of copolymers of polyamino acids and their salts as tartar barrier agents.

DESCRIPTION OF RELATED ART

U.S. Pat. No. 4,866,161 discloses polypeptides of block copolymer structure are useful for the inhibition of tartar deposition.

U.S. Pat. No. 4,339,431 discloses polypeptides of glutamic acid, tyrosine and optionally alanine are useful for the inhibition of tartar deposition.

U.S. Pat. No. 4,362,713 discloses maleic acid copolymers which are useful for the inhibition of dental plaque deposition.

U.S. Pat. No. 3,846,380 discloses the preparation and composition of copolymers of polyamino acids by the reaction of polysuccinimide with primary or secondary aliphatic amines, followed by alkaline hydrolysis to provide surface active agents. Emphasis is placed on long chain alkylamines having eight to twenty carbon atoms. The products formed are said to have good solubilizing ability, emulsifying and dispersing properties, as well as good foaming properties. They are useful as foaming agents, solubilizing agents, dispersing agents, emulsifying agents, rust-proofing agents, fiber-treating agents, level dyeing agents and retarding agents.

SUMMARY OF THE INVENTION

We have discovered that polypeptide materials that have a general formula of

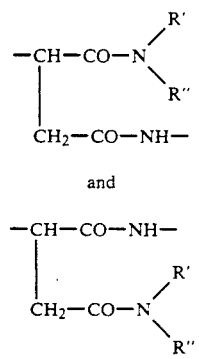

and

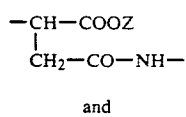

wherein R' is a hydrogen or an alkyl or alkenyl group having 1 to 20 carbons and R" is an alkyl or alkenyl group having 2 to 20 carbons, together with at least one of the groups $$-CH-COOZ$$
$$\phantom{-}|$$
$$CH_2-CO-NH-$$

and $$-CH-CO-NH-$$
$$\phantom{-}|$$
$$CH_2-COOZ$$

wherein Z represents a hydrogen atom, ammonium ion, an alkali metal or an alkaline earth metal, as a repeating unit have useful properties of inhibition of tartar deposition.

The object of this invention is to provide methods useful for inhibition of tartar deposition. Another object of this invention is to provide methods for improved oral health care.

DEFINITIONS

Polysuccinimide is the imide form of polyaspartic acid and is also known as anhydropolyaspartic acid.

The counterion, "Z" above includes, but is not limited to, hydrogen, ammonium ion, the alkali and alkaline earth metals examples of which as their cations are, $H^+$, $Na^+$, $K^+$, $Mg^+$, $Li^+$, and $Ca^{++}$, $Zn^{++}$, $Ba^{++}$, $Co^{++}$, $Fe^{++}$, $Fe^{+++}$, and $NH_4^+$.

DETAILED DESCRIPTION OF THE EMBODIMENTS

Methods of preparation of polyamino acid derivatives based upon reaction of primary or secondary amines with polysuccinimide are known as disclosed in U.S. Pat. No. 3,846,380, incorporated herein by reference. These materials were observed to have useful properties as surface active agents having no cloud point and good solubilizing, emulsifying and dispersing abilities. Thus, their use as foaming agents, solubilizing agents, dispersing agents, emulsifying agents, rust-proofing agents, fiber treating agents, level dyeing agents and retarding agents was disclosed.

The use of these agents as inhibitors of tartar deposition has hitherto been unknown. We have found that these compounds are excellent inhibitors of the formation of hydroxylapatite in vitro. This has previously been shown to correlate closely with in vivo inhibition of tartar deposition.

Such polyamino acid derivative compounds may be formulated as a dentrifice in oral hygiene formulations such as mouthwashes, rinses, irrigating solutions, abrasive gel dentrifices, nonabrasive gel dentifrices, denture cleansers, coated dental floss, interdental stimulator coatings, chewing gums, lozenges, breath fresheners, foams and sprays, as a method of delivery of said compounds for preventing tartar deposition on natural or false teeth.

The effective compounds are polyamides having in their molecules at least one of the groups

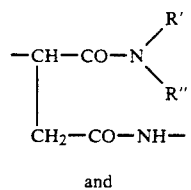

and

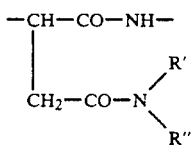

wherein R' is a hydrogen or an alkyl or alkenyl group having 1 to 20 carbons and R" is an alkyl or alkenyl group having 2 to 20 carbons, together with at least one of the groups

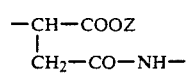

-continued and $$-CH-CO-NH- \\ | \\ CH_2-COOZ$$

wherein Z represents a hydrogen atom, an alkali metal or an alkaline earth metal, as a repeating unit.

Preferred groups for R' and R" are hydrogen, methyl, oleyl, stearyl, and lauryl.

EXAMPLE 1 pH drift assay for calcium phosphate

A solution which is supersaturated with calcium phosphate was prepared by adding 0.1 ml of previously prepared aqueous solutions of 1.32M $CaCl_2$ dihydrate and 0.90M $NaH_2PO_4$ to 29.8 ml of distilled water, resulting in 4.4 mM $Ca^{2+}$ and 3.0 mM dissolved inorganic phosphorus. The reaction vessel is closed to the atmosphere and maintained at 25° C. FIG. 1 shows a typical curve for this assay. There is considerable irregularity in the time necessary to begin precipitation and a useful endpoint is approximately 35 minutes after the assay is begun. Calcium phosphate has begun to crystalize within a few minutes of initiation (first drop in pH) and is transformed to hydroxylapatite, $Ca_{10}(PO_4)_6(OH)_2$, with a consequent downward pH drift (second drop in pH). The reaction ceases when the reactants are depleted and the pH ceases its downward drift. The results of this test with the compounds of this invention are given in Table 1. These results show that the copolymers of this invention inhibit the formation of hydroxylapatite.

TABLE 1

| compound | time to second drop in pH (min) | time to reach final pH (min) |
|---|---|---|
| blank | 14 | 23 |
| aspartate copolymer with 10% stearyl amide | >35 | — |
| aspartate copolymer with 10% oleyl amide | >35 | — |

The following examples will serve to illustrate the tartar barrier compositions of this invention. Copolymers of polyamino acids such as those described in U.S. Pat. No. 3,846,380, are suitable tartar barrier agents. Humectants are materials such as glycerol, Foaming agents are suitable surfactants. Sweetening agents may be normal or artificial sweeteners. Common abrasives are materials like fumed silica. Gelling agents are polymers which are used to prepare thickened solutions.

| | % w/w |
|---|---|
| EXAMPLE A - Mouthwash | |
| Tartar barrier agent | 0.5-2 |
| humectant | 6.0 |
| foaming agent | 1.0 |
| sweetener | 0.3 |
| deionized water | q.s. to 100 |
| flavors | 1.0 |
| EXAMPLE B - Abrasive Dentrifice Gel | |
| Tartar barrier agent | 2-10 |
| detergent | 1.5 |
| humectant | 10.0 |
| sweetener | 0.2 |
| deionized water | q.s. to 100 |

-continued

| | % w/w |
|---|---|
| flavors | 1.0 |
| abrasive | 55.0 |
| gelling agent | 2.0 |
| EXAMPLE C - Chewing gum | |
| Tartar barrier agent | 1.0-11 |
| Gum base | 21.3 |
| sugar | 48.5-58.5 |
| corn syrup | 18.2 |
| flavors | 1 |

It will be apparent to those skilled in the art that the examples and embodiments described herein are by way of illustration and not of limitation, and that other examples may be utilized without departing from the spirit and scope of the present invention, as set forth in the appended claims.

We claim:

1. A method of preventing deposition of tartar comprising treating said teeth with an effective amount of a polyamide that has a general formula of

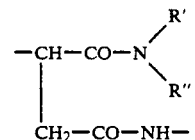

and

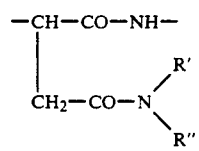

wherein R' is a hydrogen or an alkyl or alkenyl group having 1 to 20 carbons and R" is an alkyl or alkenyl group having 2 to 20 carbons, together with at least one of the groups

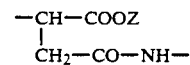

and

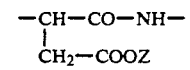

wherein Z represents a hydrogen atom, an alkali metal or an alkaline earth metal, as a repeating unit.

2. The method for preventing tartar deposition of claim 1 wherein the polyamide is a copolymer of stearyl α,β-polyaspartate amide and α,β-polyaspartic acid or its salt.

3. The method for preventing tartar deposition of claim 1 wherein the polyamide is a copolymer of oleyl α,β-polyaspartate amide and α,β-polyaspartic acid or its salt.

4. The method for preventing tartar deposition of claim 1 wherein the polyamide is a copolymer of N-methyl-N-lauryl α,β-polyaspartate amide and α,β-polyaspartic acid or its salt.

5. The method for preventing tartar deposition of claim 1 wherein the polyamide is a copolymer of lauryl α,β-polyaspartate amide and α,β-polyaspartic acid or its salt.

6. The method for preventing tartar deposition of claim 1 wherein the polyamide is a copolymer of lauryl α,β-polyaspartate amide, palmityl α,β-polyaspartate amide and α,β-polyaspartic acid or its salt.

7. A dentrifice composition, which comprises a tartar deposition inhibition effective amount of a polyamide that has a general formula of

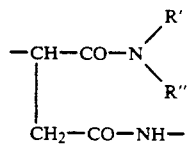

and

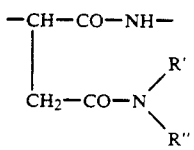

wherein R' is a hydrogen or an alkyl or alkenyl group having 1 to 20 carbons and R" is an alkyl or alkenyl group having 2 to 20 carbons, together with at least one of the groups

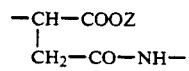

and

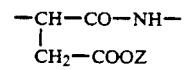

wherein Z represents a hydrogen atom, ammonia, an alkali metal or an alkaline earth metal, as a repeating unit, in combination with an orally acceptable dentrifice composition compatible with said compound.

8. A composition according to claim 7, in the form of an oral hygiene formulation selected from the group consisting of mouthwashes, rinses, irrigating solutions, abrasive gel dentrifices, nonabrasive gel dentrifices, denture cleansers, coated dental floss, interdental stimulator coatings, chewing gums, lozenges, breath fresheners, foams and sprays.

* * * * *